United States Patent
Odagami et al.

(10) Patent No.: US 10,265,331 B2
(45) Date of Patent: Apr. 23, 2019

(54) PREVENTION OR TREATMENT AGENT FOR HEPATIC FIBROSIS

(71) Applicant: PRISM Pharma Co., Ltd., Kanagawa (JP)

(72) Inventors: Takenao Odagami, Kanagawa (JP); Hiroyuki Kouji, Kanagawa (JP); Michinori Kohara, Tokyo (JP)

(73) Assignee: PRISM Pharma Co., Ltd., Kanagawa (JP)

( * ) Notice: Subject to any disclaimer, the term of this patent is extended or adjusted under 35 U.S.C. 154(b) by 0 days.

(21) Appl. No.: 15/615,131

(22) Filed: Jun. 6, 2017

(65) Prior Publication Data

US 2017/0266212 A1  Sep. 21, 2017

Related U.S. Application Data

(63) Continuation of application No. 14/651,789, filed as application No. PCT/JP2013/083339 on Dec. 12, 2013, now Pat. No. 9,700,569.

(30) Foreign Application Priority Data

Dec. 12, 2012 (JP) ................. 2012-270987

(51) Int. Cl.
*A61K 31/675* (2006.01)
*A61K 31/5365* (2006.01)
*A61K 45/06* (2006.01)
*A61K 31/53* (2006.01)

(52) U.S. Cl.
CPC ............ *A61K 31/675* (2013.01); *A61K 31/53* (2013.01); *A61K 31/5365* (2013.01); *A61K 45/06* (2013.01)

(58) Field of Classification Search
None
See application file for complete search history.

(56) References Cited

U.S. PATENT DOCUMENTS

| 7,566,711 B2 | 7/2009 | Moon et al. |
| 7,847,132 B2 | 12/2010 | Ishikawa et al. |
| 8,455,488 B2 | 6/2013 | Odagami et al. |
| 2008/0153743 A1 | 6/2008 | Henderson et al. |
| 2011/0092459 A1 | 4/2011 | Odagami et al. |
| 2016/0263131 A1 | 9/2016 | Kouji et al. |

FOREIGN PATENT DOCUMENTS

| EP | 2932977 A1 | 12/2013 |
| JP | 2008533155 T2 | 8/2008 |
| JP | 2009242374 T2 | 10/2009 |
| JP | 2009256226 A2 | 11/2009 |
| JP | 2011522037 T2 | 7/2011 |
| WO | WO 2006/101858 A1 | 9/2006 |
| WO | WO 2009/148192 A1 | 12/2009 |
| WO | WO 2011/127164 A2 | 10/2011 |
| WO | WO 2012/115286 A1 | 8/2012 |

OTHER PUBLICATIONS

Bataller, Ramon. Liver fibrosis. Journal of Clinical Investigation. 115(2), Feb. 2005, 209-218.*
Bose, S.K. et al., "Hepatitis C Virus Induces Epithelial-Mesenchymal Transition in Primary Human Hepatocytes", Journal of Virology, (Dec. 2012), vol. 86, No. 24, pp. 13621-13628.
Wu, X. et al., "Effect of Oxymatrine on the TGFbeta-Smad signaling pathway in rats with CCl4-incuded hepatic fibrosis", World J Gastroenterol, (Apr. 7, 2008), vol. 14, No. 13, pp. 2100-2105.
Guo, Y. et al., "Wnt/Beta-Catenin Signaling: a Promising New Target for Fibrosis Diseases", Physiol. Res., (2012), vol. 61, pp. 337-346.
Henderson, W. R. et al., "Inhibition of Wnt/Beta-catenin/CREB binding protein (CBP) signaling reverses pulmonary fibrosis", PNAS, (Aug. 10, 2010), vol. 107, No. 32, pp. 14309-14314.
Supplementary European Search Report dated Jul. 8, 2016 issued in EP 13 86 1603.2.
Cheng, J. H. et al., "Wnt Antagonism Inhibits Hepatic Stellate Cell Activation and Liver Fibrosis", Am. J. Phyisical Castrointest. Liver Physiol., 294, Jan. 2008, pp. G39-G49.
United States Office Action dated Jun. 19, 2017 issued in U.S. Appl. No. 15/030,095.
United States Final Office Action dated Mar. 9, 2018 issued in U.S. Appl. No. 15/030,095.
Supplementary European Search Report dated May 9, 2017 issued in EP Application No. 14 85 3712.

* cited by examiner

*Primary Examiner* — Samantha L Shterengarts
(74) *Attorney, Agent, or Firm* — Scully Scott Murphy and Presser

(57) ABSTRACT

CBP/β-catenin inhibitor shows a superior defibrosing effect for Cre/loxP/HCV-MxCre transgenic mouse which is an animal experiment model of hepatic fibrosis, and useful as a prophylactic or therapeutic drug for hepatic fibrosis.

2 Claims, 3 Drawing Sheets

HE staining (Liver)

Vehicle                    CBP/β-catenin inhibitor

PREVENTION OR TREATMENT AGENT FOR HEPATIC FIBROSIS

TECHNICAL FIELD

The present invention relates to a prophylactic or therapeutic drug for hepatic fibrosis. More particularly, the present invention relates to a prophylactic or therapeutic drug for hepatic fibrosis containing a CBP/β-catenin inhibitor.

BACKGROUND ART

Hepatic fibrosis is a condition in which production of fiber tissues called extracellular matrix composed of collagen and glycoconjugates is promoted in the process of repairing hepatocytes necrotized by various hepatic disorders such as viral hepatitis, alcoholic hepatopathy, autoimmune hepatopathy, metabolic hepatopathy and the like, and these fiber tissues are gradually accumulated along with the progression of the disease.

Particularly, after infection with hepatitis C virus (HCV), persistent infection occurs easily and chronic hepatitis is developed. Chronic hepatitis progresses to hepatic fibrosis, in which production of matrix exceeds decomposition and absorption thereof, and accumulation of fiber tissues continues, and gradually progresses to cirrhosis in which liver becomes hard due to fiber tissues.

Cirrhosis is a terminal stage symptom of chronic hepatitis, and highly frequently develops hepatocyte cancer. There is no radical cure except for liver transplantation, and development of a treatment method inducing defibrosis in the stage of hepatic fibrosis before developing cirrhosis is urgently needed.

Patent documents 1, 2 and the like disclose liver fibrosis inhibitors containing a hydroquinone derivative, proanthocyanidin and the like as an active ingredient. These known documents disclose only studies for a suppressive action on liver fibrosis at a cellular level and for an acute cirrhosis model induced by chemical substances such as carbon tetrachloride and the like, and verification using a model showing slow and sustained progression from chronic hepatitis to hepatic fibrosis and cirrhosis, which is caused by hepatitis virus, has not been performed.

DOCUMENT LIST

Patent Documents patent document 1: JP-A-2009-256226
patent document 2: JP-A-2009-242374

SUMMARY OF THE INVENTION

Problems to be Solved by the Invention

The present invention aims to provide a prophylactic or therapeutic drug for hepatic fibrosis having a superior prophylactic or therapeutic effect, particularly a prophylactic or therapeutic drug for hepatic fibrosis caused by hepatitis virus.

Means of Solving the Problems

In view of the above-mentioned problem, the present inventors have conducted intensive studies of the establishment of an appropriate animal model of hepatic fibrosis caused by hepatitis virus. As a result, they have succeeded in establishing a viral chronic hepatitis model mouse that expresses a hepatitis virus protein at an optional time, and develops chronic hepatitis, hepatic fibrosis and then cirrhosis.

Using the viral chronic hepatitis model mouse, they searched for a candidate compound for a prophylactic or therapeutic drug for hepatic fibrosis and unexpectedly found that a CBP/β-catenin inhibitor shows a superior prophylactic or therapeutic action on hepatic fibrosis, which resulted in the completion of the present invention.

Accordingly, the gist of the present invention is as described below.

[1] A prophylactic or therapeutic agent for hepatic fibrosis, comprising a CBP/β-catenin inhibitor.
[2] The prophylactic or therapeutic agent of [1], wherein the hepatic fibrosis is hepatic fibrosis caused by infection with hepatitis virus.
[3] The prophylactic or therapeutic agent of [1], wherein the hepatic fibrosis is hepatic fibrosis caused by hepatitis C or infection with hepatitis C virus.
[4] The prophylactic or therapeutic agent of any of [1] to [3], wherein the CBP/β-catenin inhibitor is a compound of the following formula (I):

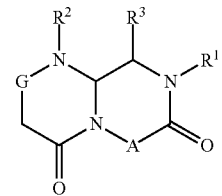

wherein
A is —CHR$^7$—
wherein
R$^7$ is hydrogen, optionally substituted alkyl, optionally substituted alkenyl, optionally substituted alkynyl, optionally substituted arylalkyl, optionally substituted heteroarylalkyl, optionally substituted cycloalkylalkyl, optionally substituted heterocycloalkylalkyl, optionally substituted aryl, optionally substituted heteroaryl, optionally substituted cycloalkyl or optionally substituted heterocycloalkyl,
G is —NH—, —NR$^6$—, —O—, —CHR$^6$— or —C(R$^6$)$_2$— wherein R$^6$ is independently selected from optionally substituted alkyl, optionally substituted alkenyl and optionally substituted alkynyl,
R$^1$ is optionally substituted arylalkyl, optionally substituted heteroarylalkyl, optionally substituted cycloalkylalkyl or optionally substituted heterocycloalkylalkyl;
R$^2$ is —W$^{21}$—W$^{22}$—Rb—R$^{20}$ wherein W$^{21}$ is —(CO)— or —(SO$_2$)—; W$^{22}$ is a bond, —O—, —NH— or optionally substituted lower alkylene;
Rb is a bond or optionally substituted lower alkylene; and
R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl, and
R$^3$ is optionally substituted alkyl, optionally substituted alkenyl or optionally substituted alkynyl, or a pharmaceutically acceptable salt thereof.
1 [5] The prophylactic or therapeutic agent of [4], wherein the CBP/β-catenin inhibitor is selected from (6S,9S)-N-benzyl-6-(4-hydroxybenzyl)-2,9-dimethyl-8-(naphthalen-1-ylmethyl)-4,7-dioxooctahydro-1H-pyrazino[2,1-c][1,2,4]triazine-1-carboxamide, (6S,9S)-2-allyl-N-benzyl-6-(4-hydroxybenzyl)-9-methyl-8-(naphthalen-1-ylmethyl)-4,7-dioxooctahydro-1H-pyrazino[2,1-c][1,2,4]triazine-1-carboxamide, (6S,9S)-N-benzyl-6-(4-hydroxybenzyl)-9-methyl-8-(naphthalen-1-ylmethyl)-4,7-dioxohexahydropyrazino[2,1-c][1,2,4]oxadiazine-1(6H)-carboxamide, (6S,9S )-8-((2-aminobenzo[d]thiazol-4-yl)methyl)-N-benzyl-6-(4-hydroxybenzyl)-2,9-dimethyl-4,7-dioxooctahydro-1H-pyrazino[2,1-c][1,2,4]triazine-1-carboxamide, (6S,9S)-N-benzyl-6-(4-hydroxybenzyl)-2,9-dimethyl-4,7-dioxo-8-(quinolin-8-ylmethyl)octahydro-1H-pyrazino[2,1-35 c][1,2,4]triazine-1-carboxamide, (6S,9S)-2-allyl-N-benzyl-6-(4-hydroxybenzyl)-9-methyl-4,7-dioxo-8-(quinolin-8-ylmethyl)octahydro-1H-pyrazino[2,1-c][1,2,4]triazine-1-carboxamide, 4-(((6S,9S)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate, 4-(((6S,9S)-1-(benzylcarbamoyl)-2,9-dimethyl-8-(naphthalen-1-ylmethyl)-4,7-dioxooctahydro-1H-pyrazino[2,1-c][1,2,4]triazin-6-yl)methyl)phenyl dihydrogen phosphate, sodium 4-(((6S,9S)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl phosphate, sodium 4-(((6S,9S)-1-(benzylcarbamoyl)-2,9-dimethyl-4,7-dioxo-8-(naphthalen-8-ylmethyl)octahydro-1H-pyrazino[2,1-c][1,2,4]triazin-6-yl)methyl)phenyl phosphate, (6S,9S)-2-allyl-6-(4-hydroxybenzyl)-9-methyl-4,7-dioxo-N-((R)-1-phenylethyl)-8-(quinolin-8-ylmethyl)octahydro-1H-pyrazino[2,1-c][1,2,4]triazine-1-carboxamide, (6S,9S)-2-allyl-6-(4-hydroxybenzyl)-9-methyl-4,7-dioxo-N-((S)-1-phenylethyl)-8-(quinolin-8-ylmethyl)octahydro-1H-pyrazino[2,1-c][1,2,4]triazine-1-carboxamide, (6S,9S)-N-benzyl-6-(4-hydroxy-2,6-dimethylbenzyl)-2,9-dimethyl-4,7-dioxo-8-(quinolin-8-ylmethyl)octahydro-1H-pyrazino[2,1-c][1,2,4]triazine-1-carboxamide, (6S,9S)-8-(benzo[b]thiophen-3-ylmethyl)-N-benzyl-6-(4-hydroxybenzyl)-2,9-dimethyl-4,7-dioxooctahydro-1H-pyrazino[2,1-c][1,2,4]triazine-1-carboxamide, (6S,9S)-8-(benzo[c][1,2,5]thiadiazol-4-ylmethyl)-N-benzyl-6-(4-hydroxybenzyl)-2,9-dimethyl-4,7-dioxooctahydro-1H-pyrazino[2,1-c][1,2,4]triazine-1-carboxamide, (6S,9S)-N-benzyl-6-(4-hydroxybenzyl)-8-(isoquinolin-5-ylmethyl)-2,9-dimethyl-4,7-dioxooctahydro-1H-pyrazino[2,1-c][1,2,4]triazine-1-carboxamide, (6S,9S)-N-benzyl-8-((5-chlorothieno[3,2-b]pyridin-3-yl)methyl)-6-(4-hydroxybenzyl)-2,9-dimethyl-4,7-dioxooctahydro-1H-pyrazino [2,1-c][1,2,4]triazine-1-carboxamide, (6S,9S)-N-benzyl-6-(4-hydroxybenzyl)-2,9-dimethyl-4,7-dioxo-8-(quinozalin-5-ylmethyl)octahydro-1H-pyrazino[2,1-c][1,2,4]triazine-1-carboxamide, and (6S,9S)-6-(4-hydroxybenzyl)-2,9-dimethyl-4,7-dioxo-8-(quinolin-8-ylmethyl)-N-(thiophen-2-ylmethyl)octahydro-1H-pyrazino[2,1-c][1,2,4]triazine-1-carboxamide.

[6] The prophylactic or therapeutic agent of [4], wherein the CBP/β-catenin inhibitor is selected from 4-(((6S,9S,9aS)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate, and (6S,9S,9aS)-N-benzyl-6-(4-hydroxybenzyl)-2,9-dimethyl-4,7-dioxo-8-(quinolin-8-ylmethyl)octahydro-1H-pyrazino[2,1-c][1,2,4]triazine-1-carboxamide.

[7] A CBP/β-catenin inhibitor used for the prophylaxis or treatment of hepatic fibrosis.

[8] The inhibitor of [7], wherein the hepatic fibrosis is caused by infection with hepatitis virus.

[9] The inhibitor of [7], wherein the hepatic fibrosis is caused by hepatitis C or infection with hepatitis C virus.

[10] A method for the prophylaxis or treatment of hepatic fibrosis, comprising administering an effective amount of a CBP/β-catenin inhibitor to a mammal.

[11] The method of [10], wherein the hepatic fibrosis is caused by infection with hepatitis virus.

[12] The method of [10], wherein the hepatic fibrosis is caused by hepatitis C or infection with hepatitis C virus.

[13] Use of a CBP/β-catenin inhibitor in the production of a prophylactic or therapeutic agent for hepatic fibrosis.

[14] The use of [13], wherein the hepatic fibrosis is caused by infection with hepatitis virus.

[15] The use of [13], wherein the hepatic fibrosis is caused by hepatitis C or infection with hepatitis C virus.

EFFECT OF THE INVENTION

According to the present invention, a prophylactic or therapeutic drug for hepatic fibrosis having a superior prophylactic or therapeutic effect can be provided.

DESCRIPTION OF EMBODIMENTS

Figure 1:
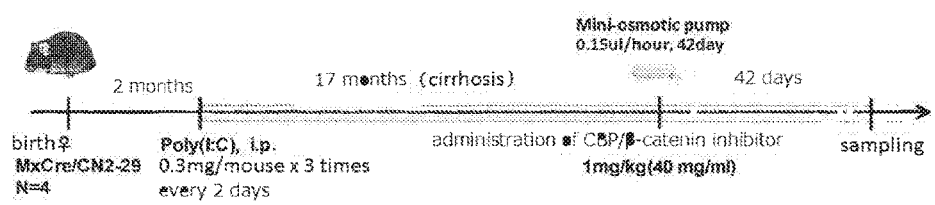
FIG. 1 shows the schedule of preparation of a hepatic fibrosis model mouse (Cre/loxP/HCV-MxCreTg mouse) and administration of a CBP/β-catenin inhibitor (Examples 1 and 2).

The present invention provides a prophylactic or therapeutic agent for hepatic fibrosis, comprising a CBP/β-catenin inhibitor. The present invention is explained in detail in the following.

(Explanation of Terms)

Unless otherwise stated, the following terms used in the specification and claims shall have the following meanings for the purposes of this Application.

"Lower", unless indicated otherwise, means that the number of the carbon atoms constituting the given radicals is between one and six (preferably between one and four).

"Optionally substituted", unless otherwise stated, means that a given radical may consist of only hydrogen substituents through available valencies or may further comprise one or more non-hydrogen substituents through available valencies. In general, a non-hydrogen substituent may be any substituent that may be bound to an atom of the given radical that is specified to be substituted. Examples of substituents include, but are not limited to, —$R^8$, —OH, —$OR^8$, —OC(O)$R^8$, —OC(O)O$R^8$, —COOH, —COO$R^8$, —CONH$_2$, —CONH$R^8$, —CON$R^8R^4$, —NH$_2$, —NH$R^8$, —N$R^8R^4$, —SH, —S$R^8$, —SO$_2R^8$, —SO$_2$NH$_2$, —SO$_2$NHR$^8$, —SO$_2$NR$^8$R$^4$ —SO$_3$H, —SOR$^8$, —NHC(NH$_2$)(=NH), —NHC(NHR$^8$)(=NR$^4$), —OP(=O)(OH)$_2$, —OP(=O)(ONa)$_2$, —OP(=O)(OR$^8$)$_2$, —OP(=O)(OR$^8$)(OH), —OP(=O)(OH)—O—P(=O)(OH)$_2$, —OP(=O)(ONa)—O—OP(=O)(ONa)$_2$, —CN, —NO$_2$ and halogen, wherein R$^8$ and R$^4$ is independently selected from linear or branched chain, cyclic or noncyclic, substituted or unsubstituted, alkyl chain, aryl and arylalkyl moieties. In addition, the substituents may be protected by a protecting group, or may itself be a protecting group.

"Halogen" means fluorine, chlorine, bromine or iodine. "Halo" means fluoro, chloro, bromo or iodo.

"Alkyl" means a linear or branched, saturated, aliphatic radical having a chain of carbon atoms. C$_{X-Y}$ alkyl is typically used where X and Y indicate the number of carbon atoms in the chain. The number of carbon atoms in the chain is preferably 1 to 10, more preferably 1 to 6, further preferably 1 to 4. Non-exclusive examples of alkyl include methyl, ethyl, propyl, isopropyl, butyl, sec-butyl, isobutyl, tert-butyl, pentyl, isopentyl, neopentyl, tert-pentyl, hexyl, isohexyl and the like.

"Alkenyl" means a linear or branched, carbon chain that contains at least one carbon-carbon double bond. C$_{X-Y}$ alkenyl is typically used where X and Y indicate the number of carbon atoms in the chain. The number of carbon atoms in the chain is preferably 2 to 10, more preferably 2 to 6, further preferably 2 to 4. Non-exclusive examples of alkenyl include ethenyl (vinyl), allyl, isopropenyl, 2-methylallyl, 1-pentenyl, hexenyl, heptenyl, 1-propenyl, 2-butenyl, 2-methyl-2-butenyl, and the like.

"Alkynyl" means a linear or branched, carbon chain that contains at least one carbon-carbon triple bond. C$_{X-Y}$ alkynyl is typically used where X and Y indicate the number of carbon atoms in the chain. The number of carbon atoms in the chain is preferably 2 to 10, more preferably 2 to 6, further preferably 2 to 4. Non-exclusive examples of alkynyl include ethynyl, propargyl, 3-methyl-1-pentynyl, 2-heptynyl and the like.

"Alkylene", unless indicated otherwise, means a linear or branched, saturated, aliphatic, polyvalent carbon chain. C$_{X-Y}$ alkylene is typically used where X and Y indicate the number of carbon atoms in the chain. The number of carbon atoms in the chain is preferably 1 to 10, more preferably 1 to 6, further preferably 1 to 4. Non-exclusive examples of alkylene include methylene (—CH$_2$—), ethylene (—CH$_2$CH$_2$—), methylmethylene (—CH(CH$_3$)—), 1,2-propylene (—CH$_2$CH(CH$_3$)—), 1,3-propylene (—CH$_2$CH$_2$CH$_2$—), 1,2-butylene (—CH$_2$CH(CH$_2$CH$_3$)—), 1,3-butylene (—CH$_2$CH$_2$CH(CH$_3$)—), 1,4-butylene (—CH$_2$CH$_2$CH$_2$CH$_2$—), 2-methyltetramethylene (—CH$_2$CH(CH$_3$)CH$_2$CH$_2$—), pentamethylene (—CH$_2$CH$_2$CH$_2$CH$_2$CH$_2$—), 1,2,3-propanetriyl, 1,3,3-propanetriyl and the like.

"Oxy" means the radical —O—. It is noted that the oxy radical may be further substituted with a variety of substituents to form different oxy groups including hydroxy, alkoxy, aryloxy, heteroaryloxy and the like.

"Thio" means the radical —S—. It is noted that the thio radical may be further substituted with a variety of substituents to form different thio groups including mercapto, alkylthio, arylthio, heteroarylthio and the like.

"Sulfinyl" means the radical —SO—. It is noted that the sulfinyl radical may be further substituted with a variety of substituents to form different sulfinyl groups including alkylsulfinyl, arylsulfinyl, heteroarylsulfinyl and the like.

"Sulfonyl" means the radical —SO$_2$—. It is noted that the sulfonyl radical may be further substituted with a variety of substituents to form different sulfonyl groups including alkylsulfonyl, arylsulfonyl, heteroarylsulfonyl and the like.

"Alkoxy" means an oxygen moiety having a further alkyl substituent. C$_{X-Y}$ alkoxy is typically used where X and Y indicate the number of carbon atoms in the chain. The number of carbon atoms in the chain is preferably 1 to 10, more preferably 1 to 6, further preferably 1 to 4. Non-exclusive examples of alkoxy include methoxy, ethoxy, propoxy, isopropoxy, butoxy, sec-butoxy, isobutoxy, tert-butoxy, pentoxy, isopentoxy, neopentoxy, tert-pentoxy, hexyloxy, isohexyloxy, and the like.

"Heteroatom" refers to an atom that is not a carbon atom and hydrogen atom. Particular examples of heteroatoms include, but are not limited to nitrogen, oxygen, and sulfur.

"Aryl" means a monocyclic or polycyclic (e.g., bicyclic, tricyclic) radical wherein each ring is aromatic or when fused with one or more rings forms an aromatic ring. C$_{X-Y}$ aryl is typically used where X and Y indicate the number of carbon atoms in the ring assembly. The number of carbon atoms in the ring is preferably 6 to 14, more preferably 6 to 10. Non-exclusive examples of aryl include phenyl, naphthyl, indenyl, azulenyl, biphenyl, fluorenyl, anthracenyl, phenalenyl and the like.

"Heteroaryl" means a monocyclic or polycyclic aromatic radical wherein at least one ring atom is a heteroatom and the remaining ring atoms are carbon. "X-Y membered heteroaryl" is typically used where X and Y indicate the number of carbon atoms and heteroatoms in the ring assembly. The number of carbon atoms and heteroatoms in the ring is preferably 5 to 14, more preferably 5 to 10. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Non-exclusive examples of monocyclic heteroaryl group of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrrole, triazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, and another monocyclic heteroaryl or heterocycloalkyl ring. Non-exclusive examples of bicyclic or tricyclic heteroaryl include, but are not limited to, those derived from benzofuran (ex. benzo[b]furan), benzothiophene (ex. benzo[b]thiophene), benzimidazole, benzotriazine (ex. benzo[e][1,2,4]triazine, benzo[d][1,2,3]triazine), pyridopyrimidine (ex. pyrido[4,3-d]pyrimidine, pyrido[3,4-d]pyrimidine, pyrido[3,2-d]pyrimidine, pyrido[2,3-d]pyrimidine), pyridopyrazine (ex. pyrido[3,4-b]pyrazine, pyrido[2,3-b]pyrazine), pyridopyridazine (ex. pyrido[2,3-c]pyridazine, pyrido[3,4-c]pyridazine, pyrido[4,3-c]pyridazine, pyrido[3,2-c]pyridazine), pyridotriazine (ex. pyrido[2,3-d][1,2,3]triazine, pyrido[3,4-d][1,2,3]triazine, pyrido[4,3-d][1,2,3]triazine, pyrido[3,2-d][1,2,3]triazine, pyrido[3,4-e][1,2,4]triazine, pyrido[3,2-e][1,2,4]triazine), benzothiadiazole (ex. benzo[c][1,2,5]thiadiazole), furopyridine (ex. furo[3,2-b]pyridine, furo[3,2-c]pyridine, furo[2,3-c]pyridine, furo[2,3-b]pyridine), oxazolopyridine (ex. oxazolo[4,5-b]pyridine, oxazolo[4,5-c]pyridine, oxazolo[5,4-c]pyridine, oxazolo[5,4-b]pyridine), thiazolopyridine (ex. thiazolo[4,5-b]pyridine, thiazolo[4,5-c]pyridine, thiazolo[5,4-c]pyridine, thiazolo[5,4-b]pyridine), imidazopyridine (ex. imidazo[1,2-a]pyridine, imidazo[4,5-c]pyridine, imidazo[1, 5-a]pyridine), quinazoline, thienopyridine (ex. thieno[2,3-c]pyridine, thieno[3,2-b]pyridine, thieno[2,3-b]pyridine), indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine (ex. pyrazolo[1,5-a]pyridine), imidazopyrimidine (ex. imidazo[1,2-a]pyrimidine, imidazo[1,2-c]pyrimidine, imidazo[1,5-a]pyrimidine, imidazo[1,5-c]pyrimidine), pyrrolopyridine (ex. pyrrolo[2,3-b]pyridine, pyrrolo[2,3-c]pyridine, pyrrolo[3,2-c]pyridine, pyrrolo[3,2-b]pyridine), pyrrolopyrimidine (ex. pyrrolo[2,3-d]pyrimidine, pyrrolo[3,2-d]pyrimidine, pyrrolo[1,2-c]pyrimidine, pyrrolo[1,2-a]pyrimidine), pyrrolopyrazine (ex. pyrrolo[2,3-b]pyrazine, pyrrolo[1,2-a]pyrazine), pyrrolopyridazine (ex. pyrrolo[1,2-b]pyridazine), triazopyridine (ex. triazo[1,5-a]pyridine), pteridine, purine, carbazole, acridine, permidine, 1,10-phenanthroline, phenoxathiin, phenoxazine, phenothiazine, phenazine and the like. The bicyclic or tricyclic heteroaryl rings can be attached to the parent molecule through either the heteroaryl group itself or the aryl, cycloalkyl, or heterocycloalkyl group to which it is fused.

"Cycloalkyl" means a non-aromatic, saturated or partially unsaturated, monocyclic, fused bicyclic or bridged polycyclic ring radical. $C_{X-Y}$ cycloalkyl is typically used where X and Y indicate the number of carbon atoms in the ring assembly. The number of carbon atoms in the ring is preferably 3 to 10, more preferably 3 to 8. Non-exclusive examples of heterocycloalkyl include cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, bicyclo[2.2.1]hept-1-yl, and the like.

"Heterocycloalkyl" means cycloalkyl, as defined in this Application, provided that one or more of the atoms forming the ring is a heteroatom selected, independently from N, O, or S. $C_{X-Y}$ heterocycloalkyl is typically used where X and Y indicate the number of carbon atoms and heteroatoms in the ring assembly. The number of carbon atoms and heteroatoms in the ring is preferably 3 to 10, more preferably 3 to 8. Non-exclusive examples of heterocycloalkyl include piperidyl, 4-morpholyl, 4-piperazinyl, pyrrolidinyl, perhydropyrrolidinyl, 1,3-dioxanyl, 1,4-dioxanyl, and the like.

Moreover, the above-mentioned definitions can apply to groups wherein the above-mentioned substituents are connected. For example, "arylalkyl" means linear or branched alkyl group which is substituted by aryl groups, such as benzyl, 1-phenylethyl, 2-phenylethyl, 3-phenylpropyl, 1-naphthylmethyl, 2-naphthylmethyl and the like.

"Fused ring" as used herein refers to an assembly of plural rings wherein the ring is bonded to another ring when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated or aromatic.

"Bridging ring" as used herein refers to a ring that is bonded to another ring to form a compound having a bicyclic structure where two ring atoms that are common to both rings are not directly bound to each other. Non-exclusive examples of common compounds having a bridging ring include adamantine, borneol, norbornane, 7-oxabicyclo[2.2.1]heptane, and the like.

"Protected derivatives" mean derivatives of compound in which a reactive site or sites are blocked with protecting groups. A comprehensive list of suitable protecting groups can be found in T.W. Greene, *Protecting Groups in Organic Synthesis,* 3rd edition, John Wiley & Sons, Inc. 1999.

"Isomers" mean any compound having an identical molecular formula but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R-and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Animal" includes humans, non-human mammals (e.g., mice, rats, hamsters, dogs, cats, rabbits, cattle, horses, sheep, goats, swine, monkeys, deer, and the like) and non-mammals (e.g., birds, and the like).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salt" or "salt" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tert-butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide.

Acceptable organic bases include ethanolamine, diethanolamine, triethanolamine, tromethamine, N-methylglucamine and the like.

It is noted in regard to all of the definitions provided herein that the definitions should be interpreted as being open ended in the sense that further substituents beyond those specified may be included.

(Hepatic Fibrosis)

Hepatic fibrosis is a condition in which production of fiber tissues called extracellular matrix composed of collagen and glycoconjugates is promoted in the process of repairing hepatocytes necrotized by various hepatic disorders such as viral hepatitis, alcoholic hepatopathy, autoimmune hepatopathy, metabolic hepatopathy and the like, and these fiber tissues are gradually accumulated along with the progression of the inflammation.

While hepatic disorder causing hepatic fibrosis is not particularly limited, viral hepatitis, alcoholic hepatopathy, autoimmune hepatopathy, drug-induced hepatopathy, metabolic hepatopathy (fatty liver, nonalcoholic steatohepatitis, hemochromatosis) and the like can be mentioned. Hepatic fibrosis to be the target in the prophylaxis or treatment of the present invention is preferably one caused by viral hepatitis.

The pathogenic virus of viral hepatitis is not particularly limited, and hepatitis A virus, hepatitis B virus, hepatitis C virus, hepatitis E virus and the like can be mentioned. Of these, an embodiment wherein hepatic fibrosis is developed via hepatitis C caused by hepatitis C virus is preferable.

The "treatment of hepatic fibrosis" means complete cure of the pathology of hepatic fibrosis, as well as suppression of the progression or exacerbation of the symptoms to prevent progression of the pathology, even though it may not be a complete cure, or improvement of a part of or whole pathology to lead to the direction of cure.

The "prophylaxis of hepatic fibrosis" means prevention, suppression or delay of the onset of the pathology of hepatic fibrosis.

The "effective amount for the treatment of hepatic fibrosis" means an amount sufficient for achieving such treatment of hepatic fibrosis when administered to an animal to treat hepatic fibrosis.

The "effective amount for the prophylaxis of hepatic fibrosis" means an amount sufficient for achieving such prophylaxis of hepatic fibrosis when administered to an animal to prevent hepatic fibrosis.

(CBP/β-Catenin Inhibitor)

β-catenin acts as a mediator of Wnt signal transduction, binds to a transcription factor Tcf/Lef (T cell factor/Lymphocyte enhancing factor), promotes expression of various genes (cyclin D1, c-Myc etc.) relating to Wnt signal transduction, and controls growth and differentiation of the cells (He et al., 1998 Science 281 1509-1512: Kolligs et al., 1999 Mol. Cell. Biol. 19, 5696-5706: Crawford et al., 1999, Oncogene 18, 2883-2891: Shtutman et al., 1999, Proc. Natl. Acad. Sci. USA., 11, 5522-5527: Tetsu and McCormick, 1999 Nature, 398, 422-426).

CBP (cyclic AMP reactive element binding protein (CREB) binding protein) directly interacts with β-catenin in the CREB binding domain, and promotes transcription activation of Tcf/Lef (Ken-Ichi Takemaru and Randall T. Moon, 2000 J. Cell. Biol., 149, 2, 249-254).

The CBP/β-catenin inhibitor is not particularly limited as long as it inhibits interaction of CBP and β-catenin, and an embodiment wherein it inhibits binding of β-catenin and CBP and, as a result, suppresses gene expression by β-catenin complex is preferable.

While CBP/β-catenin inhibition can be measured by a binding assay known per se (radiobinding assay etc.), reporter assay method and the like, it can be preferably confirmed by measuring the gene expression of Wnt signal transduction by the reporter assay method described in WO 2009/148192.

While the CBP/β-catenin inhibitor of the present invention is not particularly limited as long as it is as defined above, for example, an antibody (polyclonal antibody, monoclonal antibody) having affinity to CBP and/or β-catenin, the compounds described in WO 2003/031448, WO 2004/093828, WO 2005/116032, WO 2009/148192, WO 2010/044485, WO 2010/128685, WO 2012/115286 and the like, a pharmaceutically acceptable salt thereof and the like can be mentioned.

As a preferable embodiment of the CBP/β-catenin inhibitor of the present invention, a compound having the following formula (I) or a pharmaceutically acceptable salt thereof can be mentioned.

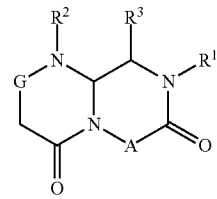

wherein

A is —CHR$^7$— wherein

R$^7$ is hydrogen, optionally substituted alkyl, optionally substituted alkenyl, optionally substituted alkynyl, optionally substituted arylalkyl, optionally substituted heteroarylalkyl, optionally substituted cycloalkylalkyl, optionally substituted heterocycloalkylalkyl, optionally substituted aryl, optionally substituted heteroaryl, optionally substituted cycloalkyl or optionally substituted heterocycloalkyl, G is —NH—, —NR$^6$—, —O—, —CHR$^6$— or —C(R$^6$)$_2$— wherein R$^6$ is independently selected from optionally substituted alkyl, optionally substituted alkenyl and optionally substituted alkynyl, R$^1$ is optionally substituted arylalkyl, optionally substituted heteroarylalkyl, optionally substituted cycloalkylalkyl or optionally substituted heterocycloalkylalkyl;

R$^2$ is —W$^{21}$—W$^{22}$—Rb—R$^{20}$ wherein W$^{21}$ is —(CO)— or —(SO$_2$)—; W$^{22}$ is a bond, —O—, —NH— or optionally substituted lower alkylene;

Rb is a bond or optionally substituted lower alkylene; and

R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl, and R$^3$ is optionally substituted alkyl, optionally substituted alkenyl or optionally substituted alkynyl.

The compound of the formula (I) can be produced according to the method described in WO 2009/148192.

In the above-mentioned formula (I), an embodiment having the following substituents is more preferable.

A compound having the formula (I) wherein

A is —CHR$^7$— wherein

R⁷ is optionally substituted arylalkyl, optionally substituted heteroarylalkyl, optionally substituted cycloalkylalkyl, or optionally substituted heterocycloalkylalkyl);

G is —NH—, —NR⁶—, or —O—
wherein
R⁶ is lower alkyl, or lower alkenyl);
R¹ is —Ra—R¹⁰
wherein
Ra is optionally substituted lower alkylene, and
R¹⁰ is optionally substituted bicyclic fused aryl, or optionally substituted bicyclic fused heteroaryl;
R² is —(CO)—NH—Rb—R²⁰
wherein
Rb is a bond or optionally substituted lower alkylene, and
R²⁰ is optionally substituted aryl, or optionally substituted heteroaryl); and
R³ is $C_{1-4}$ alkyl,
or a pharmaceutically acceptable salt thereof.

In the above-mentioned formula (I), an embodiment having the following substituents is further preferable.

A compound having the formula (I) wherein
A is —CHR⁷—
wherein
R⁷ is arylalkyl optionally substituted by hydroxy or $C_{1-4}$ alkyl;
G is —NH—, —NR⁶—, or —O—
wherein
R⁶ is $C_{1-4}$ alkyl, or $C_{2-4}$ alkenyl;
R¹ is —Ra—R¹⁰
wherein
Ra is $C_{1-4}$ alkylene, and
R¹⁰ is bicyclic fused aryl, or bicyclic fused heteroaryl optionally substituted by halogen or amino;
R² is —(CO)—NH—Rb—R²⁰
wherein
Rb is a bond or $C_{1-4}$ alkylene, and
R²⁰ is aryl, or heteroaryl; and
R³ is $C_{1-4}$ alkyl,
or a pharmaceutically acceptable salt thereof.

Specific preferable examples of the CBP/β-catenin inhibitor of the present invention include the following compounds.

(6S,9S)-N-benzyl-6-(4-hydroxybenzyl)-2,9-dimethyl-8-(naphthalene-1-ylmethyl)-4,7-dioxooctahydro-1H-pyrazino[2,1-c][1,2,4]triazine-1-carboxamide, (6S,9S)-2-allyl-N-benzyl-6-(4-hydroxybenzyl)-9-methyl-8-(naphthalen-1-ylmethyl)-4,7-dioxooctahydro-1H-pyrazino[2,1-c][1,2,4]triazine-1-carboxamide, (6S,9S)-N-benzyl-6-(4-hydroxybenzyl)-9-methyl-8-(naphthalen-1-ylmethyl)-4,7-dioxohexahydropyrazino[2,1-c][1,2,4]oxadiazine-1(6H)-carboxamide, (6S,9S)-8-((2-aminobenzo[d]thiazol-4-yl)methyl)-N-benzyl-6-(4-hydroxybenzyl)-2,9-dimethyl-4,7-dioxooctahydro-1H-pyrazino[2,1-c][1,2,4]triazine-1-carboxamide, (6S,9S)-N-benzyl-6-(4-hydroxybenzyl)-2,9-dimethyl-4,7-dioxo-8-(quinolin-8-ylmethyl)octahydro-1H-pyrazino[2,1-c][1,2,4]triazine-1-carboxamide, (6S,9S)-2-allyl-N-benzyl-6-(4-hydroxybenzyl)-9-methyl-4,7-dioxo-8-(quinolin-8-ylmethyl)octahydro-1H-pyrazino[2,1-c][1,2,4]triazine-1-carboxamide, 4-(((6S,9S)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate, 4-(((6S,9S)-1-(benzylcarbamoyl)-2,9-dimethyl-8-(naphthalen-1-ylmethyl)-4,7-dioxooctahydro-1H-pyrazino[2,1-c][1,2,4]triazin-6-yl)methyl)phenyl dihydrogen phosphate, sodium 4-(((6S,9S)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl phosphate, sodium 4-(((6S,9S)-1-(benzylcarbamoyl)-2,9-dimethyl-4,7-dioxo-8-(naphthalen-8-ylmethyl)octahydro-1H-pyrazino[2,1-c][1,2,4]triazin-6-yl)methyl)phenyl phosphate, (6S,9S)-2-allyl-6-(4-hydroxybenzyl)-9-methyl-4,7-dioxo-N-((R)-1-phenylethyl)-8-(quinolin-8-ylmethyl)octahydro-1H-pyrazino[2,1-c][1,2,4]triazine-1-carboxamide, (6S,9S)-2-allyl-6-(4-hydroxybenzyl)-9-methyl-4,7-dioxo-N-((S)-1-phenylethyl)-8-(quinolin-8-ylmethyl)octahydro-1H-pyrazino[2,1-c][1,2,4]triazine-1-carboxamide, (6S,9S)-N-benzyl-6-(4-hydroxy-2,6-dimethylbenzyl)-2,9-dimethyl-4,7-dioxo-8-(quinolin-8-ylmethyl)octahydro-1H-pyrazino[2,1-c][1,2,4]triazine-1-carboxamide, (6S,9S)-8-(benzo[b]thiophen-3-ylmethyl)-N-benzyl-6-(4-hydroxybenzyl)-2,9-dimethyl-4,7-dioxooctahydro-1H-pyrazino[2,1-c][1,2,4]triazine-1-carboxamide, (6S,9S)-8-(benzo[c][1,2,5]thiadiazol-4-ylmethyl)-N-benzyl-6-(4-hydroxybenzyl)-2,9-dimethyl-4,7-dioxooctahydro-1H-pyrazino[2,1-c][1,2,4]triazine-1-carboxamide, (6S,9S)-N-benzyl-6-(4-hydroxybenzyl)-8-(isoquinolin-5-ylmethyl)-2,9-dimethyl-4,7-dioxooctahydro-1H-pyrazino[2,1-c][1,2,4]triazine-1-carboxamide, (6S,9S)-N-benzyl-8-((5-chlorothieno[3,2-b]pyridin-3-yl)methyl)-6-(4-hydroxybenzyl)-2,9-dimethyl-4,7-dioxooctahydro-1H-pyrazino[2,1-c][1,2,4]triazine-1-carboxamide, (6S,9S)-N-benzyl-6-(4-hydroxybenzyl)-2,9-dimethyl-4,7-dioxo-8-(quinozalin-5-ylmethyl)octahydro-1H-pyrazino[2,1-c][1,2,4]triazine-1-carboxamide, and (6S,9S)-6-(4-hydroxybenzyl)-2,9-dimethyl-4,7-dioxo-8-(quinolin-8-ylmethyl)-N-(thiophen-2-ylmethyl)octahydro-1H-pyrazino[2,1-c][1,2,4]triazine-1-carboxamide.

The most preferably embodiment of the CBP/β-catenin inhibitor of the present invention is 4-(((6S,9S,9aS)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate, or (6S,9S,9aS)-N-benzyl-6-(4-hydroxybenzyl)-2,9-dimethyl-4,7-dioxo-8-(quinolin-8-ylmethyl)octahydro-1H-pyrazino[2,1-c][1,2,4]triazine-1-carboxamide.

(Hepatic Fibrosis Model Mouse)

The present inventors produced, as an animal model capable of accurately evaluating chronic hepatitis C in human, a transgenic mouse (Cre/loxP/HCV-MxCreTg mouse) capable of switching expression of HCV gene at an optional time by mating a transgenic (Cre/loxP/HCV-Tg) mouse introduced with an HCV gene by the Cre/loxP system, and a transgenic (Mx-Cre-Tg) mouse capable of expressing IFN-inducible Cre. When polyinosinic-polycytidylic acid (Poly(I:C)) is administered to this Tg mouse, IFNα-inducible Cre enzyme is expressed, which loops out a neomycin resistance gene sandwiched between loxP sequences, whereby HCV protein can be expressed at an optional time. That is, since the switching expression system was established, expression of HCV gene no longer occurred in the developmental stage, and an immune reaction state similar to HCV infection was successfully produced.

The HCV protein in the liver, which was expressed by the administration of Poly(I:C) to the model mouse was not completely eliminated and sustained expression for 600 days or longer was confirmed. Morphologically, hepatocyte swelling, fat denaturation, glycogene denaturation, turbulence of hepatocyte cord, fibrosis, hepatocyte cancer and lymphoma and the like were observed.

Therefore, the Cre/loxP/HCV-MxCre Tg mouse is a pathology model capable of accurately evaluating the pathology from hepatitis C to hepatic fibrosis, cirrhosis, and to liver cancer.

(Pharmaceutical Preparation Containing CBP/β-Catenin Inhibitor)

The CBP/β-catenin inhibitor of the present invention can be administered to human or animal (e.g., mammals such as mouse, rat, hamster, rabbit, cat, dog, bovine, sheep, monkey and the like) as a pharmaceutical preparation (e.g., injection, capsule, tablet, powder, granule and the like) formulated by a conventional method. For example, it is preferably administered at a dose in the amount of the active ingredient of about 0.01-1000 mg/kg (body weight) per day, preferably about 0.1-500 mg/kg (body weight) per day, in one to several portions. The dose thereof, administration method and administration frequency may vary as appropriate depending on the symptom, age and the like. For example, for formulation into injection, carriers such as distilled water, saline and the like may be used and, for formulation into capsule, tablet, powder, granule, excipients such as starch, lactose, sucrose, calcium carbonate and the like, binders such as starch paste, gum arabic, gelatin, sodium alginate, carboxymethylcellulose, hydroxypropylcellulose and the like, lubricants such as magnesium stearate, talc and the like, disintegrants such as starch, agar, crystalline cellulose, calcium carbonate, sodium hydrogen carbonate, sodium alginate and the like, and the like can be used. The content of the active ingredient in a preparation can vary between 1-99 wt %. For example, the dosage form of tablet, capsule, granule, powder and the like preferably contain 5-80 wt % of the active ingredient, and injection preferably contains 1-10 wt % of the active ingredient.

While the administration method is not particularly limited, oral administration, intravenous administration, intravenous sustained administration, intraperitoneal administration and the like can be mentioned.

Also, an embodiment wherein an osmotic pressure pump filled with the pharmaceutical composition of the present invention is, for example, subcutaneously embedded for administration in a sustained manner is preferable.

EXAMPLES

The present invention is explained in more detail in the following by referring to Examples, which are not to be construed as limitative in any way.

Example 1

Production of Hepatic Fibrosis Model Mouse

R6CN2 HCV cDNA (nt 294-3435) and whole genome HCV cDNA (nt 1-9611) were cloned from blood samples collected from patients (#R6) affected with chronic active hepatitis. The infection of the blood samples was measured according to the method reported in a known document (Proc. Natl. Acad. Sci. USA, 90: 6037-6041). R6CN2HCV and R6CN5HCV transgenic mice were crossed with Mx1-Cre transgenic mouse (purchased from Jackson Laboratory) to produce R6CN2HCV-MxCre transgenic mouse and R6CN5HCV-MxCre transgenic mouse, which were named CN2-29$^{(+/-)}$/MxCre$^{(+/-)}$ mouse and RzCN5-15$^{(+/-)}$/MxCre$^{(+/-)}$ mouse, respectively.

The expression of Cre in the liver of these mice was induced by intraperitoneal injection of polyinosinic-polycytidylic acid [Poly(I:C)] (purchased from GE Healthcare UK Ltd. (Buckinghamshire, England)). That is, 300 μL of poly(I:C) solution (1 mg/mL phosphate buffered saline [PBS]) was intraperitoneally injected, after lapse of 2 months from birth, 35 3 times at 48 hr intervals. HCV gene expression can be induced in almost all hepatocytes by performing this poly(I:C) administration operation once. The expression persists for not less than 600 days, and a hepatic fibrosis animal model that shows from chronic hepatitis to liver fibrosis could be established.

The all animal care and experiment procedures were performed according to the guideline established by Tokyo Metropolitan Institute of Medical Science Subcommittee on Laboratory Animal Care.

Example 2

Treatment Effect of CBP/β-Catenin Inhibitor

A CBP/β-catenin inhibitor was intraperitoneally administered to the CN2-29$^{(+/-)}$/MxCre$^{(+/-)}$ mouse obtained in Example 1, and whether the CBP/β-catenin inhibitor has a treatment effect on hepatic fibrosis was examined by histological staining of the hepatic tissues collected from the model mouse.

(1) Preparation And administration of CBP/β-catenin Inhibitor

A CBP/β-catenin inhibitor was dissolved in commercially available PBS (pH 7.6), and the pH was adjusted again to 7.6 with an aqueous sodium hydroxide solution to give a 40 mg/ml CBP/β-catenin inhibitor solution. This solution (250 μl) was filled in an osmotic pressure pump (ALZET mini-osmotic pump model 2006) and embedded subcutaneously in the back of mouse, whereby a CBP/β-catenin inhibitor was administered at 0.15 μl/hr for 42 days in a sustained manner. For the control group, commercially available PBS (pH7.6) was similarly filled in an osmotic pressure pump and administered as a vehicle by embedding same subcutaneously in the back of mouse. The schedule of production of a model and administration of a CBP/β-catenin inhibitor is shown in FIG. 1.

The CBP/β-catenin inhibitor used in this Example was as described below:

4-(((6S,9S)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate (hereinafter to be simply referred to as "CBP/β-catenin inhibitory compound").

The CBP/β-catenin inhibitory compound is the compound described in Example I-7 of WO 2009/148192, and can be synthesized by the method described in the document. A CBP/β-catenin inhibitory action of the CBP/β-catenin inhibitory compound has been confirmed by the reporter assay method described in the document.

(2) Histological Staining

Autopsy was performed on day 42 from the administration of the CBP/β-catenin inhibitory compound of (1), the liver was removed and histologically searched.

As for staining, the whole image of the tissue was stained and observed by hematoxylin-eosin staining (HE staining), and fiber was stained and observed by silver staining and Azan staining.

Hematoxylin-eosin staining is the most basic and important general staining method for pathological tissues, and aims to grasp the whole image of a tissue structure at a light microscopic level. Using each staining solution of hematoxylin and eosin, dyeing in different colors is performed as follows.

livid to light blue by hematoxylin: cell nuclei, calcareous parts, cartilaginous tissue, bacteria, mucosa.

red to dark red by eosin: cytoplasm, interstitial tissues, various fibers, erythrocytes, keratinocytes.

Silver staining aims to stain reticular fiber which is one of the binding tissue fibers.

Azan staining is a staining method to dye in different colors for collagenous fibers (dark blue) and muscle fibers (blue).

Specific method is as described below.

A tissue sample was fixed with 4% para-formaldehyde in PBS, embedded in paraffin and sliced (thickness 4 μm). The obtained section was subjected to hematoxylin-eosin staining (HE), silver staining and Azan staining.

Hematoxylin-eosin staining was performed according to the method described in a handbook of histopathological staining (Kiyoyuki Takahashi, Igaku-Shoin).

Silver staining was performed according to the method described in a handbook of histopathological staining (Kiyoyuki Takahashi, Igaku-Shoin).

Azan staining was performed according to the method described in a handbook of histopathological staining (Kiyoyuki Takahashi, Igaku-Shoin).

Figure 2:
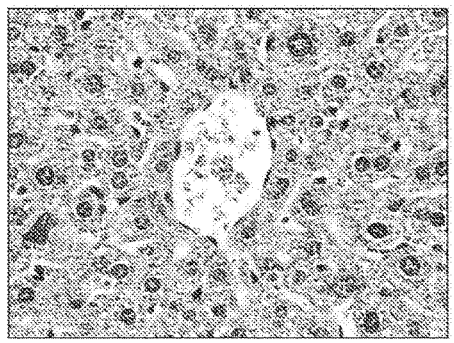
FIG. 2 shows liver histological staining (hematoxylin-eosin staining) when a CBP/β-catenin inhibitor is administered to a hepatic fibrosis model mouse (Cre/loxP/HCV-MxCreTg mouse).
Figure 2:
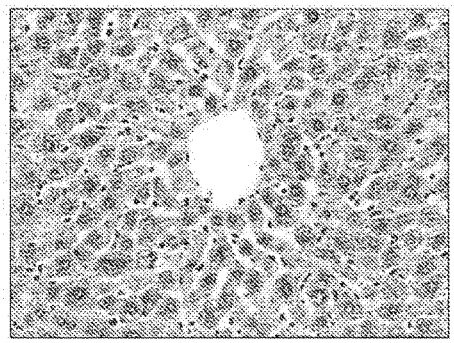
Figure 3:
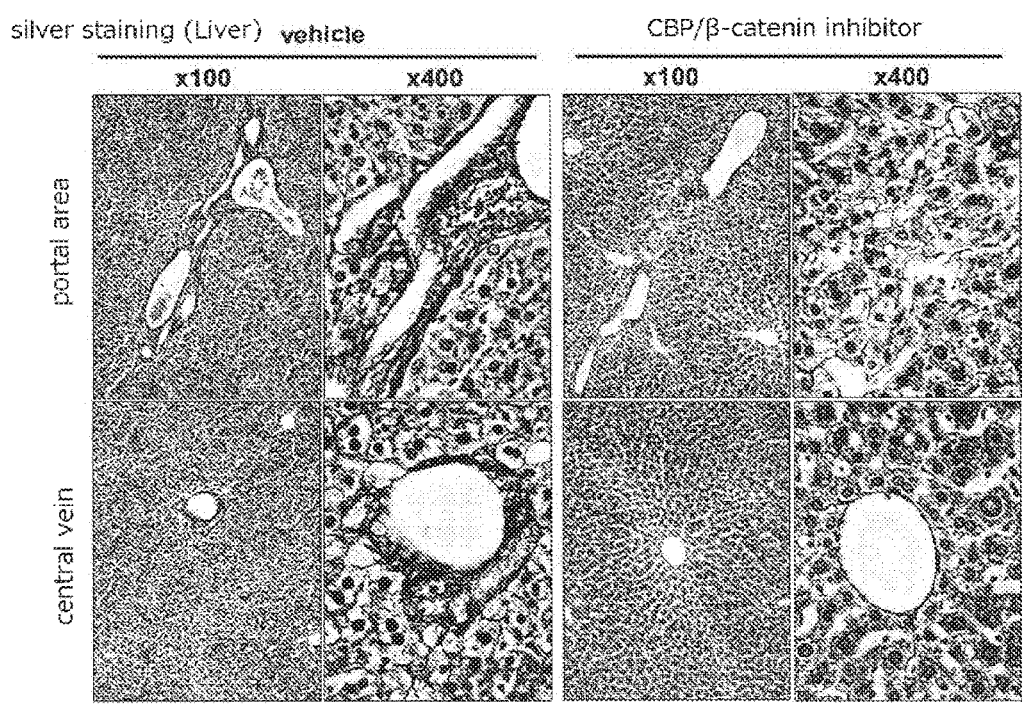
FIG. 3 shows liver histological staining (silver staining) when a CBP/β-catenin inhibitor is administered to a hepatic fibrosis model mouse (Cre/loxP/HCV-MxCreTg mouse).
Figure 4:
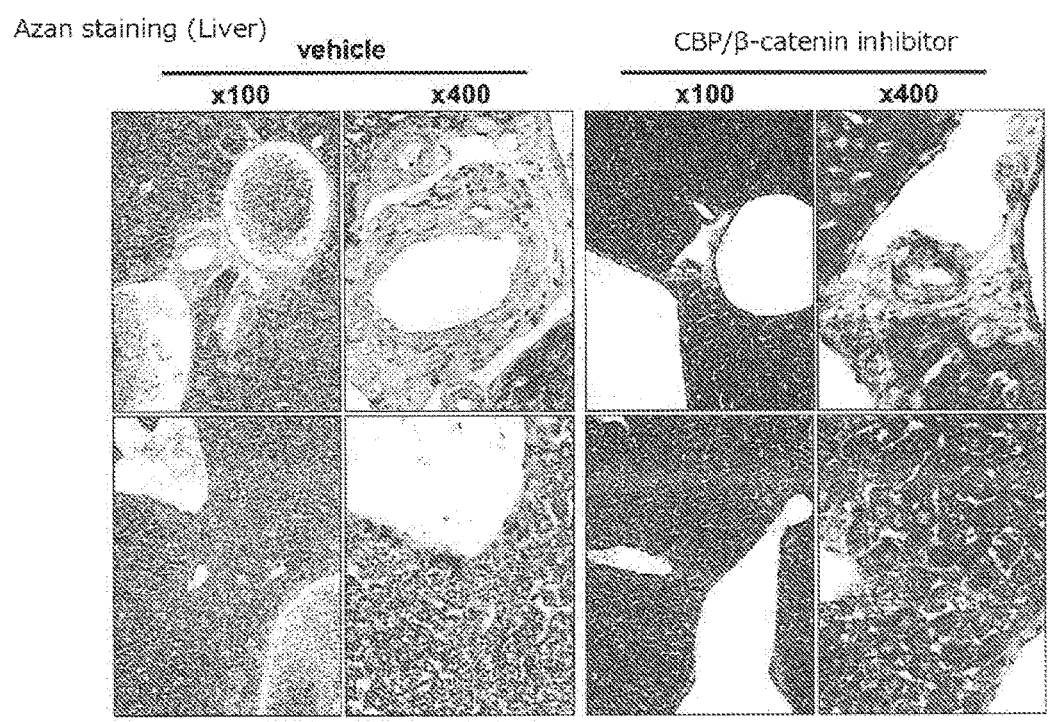
FIG. 4 shows liver histological staining (Azan staining) when a CBP/β-catenin inhibitor is administered to a hepatic fibrosis model mouse (Cre/loxP/HCV-MxCreTg mouse).

The results are shown in FIG. 2 (HE staining), FIG. 3 (silver staining) and FIG. 4 (Azan staining).

The CBP/β-catenin inhibitory compound improved hepatic lobule structure of chronic hepatitis C model mouse (Cre/loxP/HCV-MxCre Tg mouse) by administration for 42 days, thus showing a defibrosing action (FIG. 2, FIG. 3, FIG. 4).

Liver tissue abnormally grown due to chronic hepatitis and having no hepatocyte cord structure was normalized to take a cord-like form by the administration of a CBP/β-catenin inhibitory compound (FIG. 2).

Due to chronic hepatitis, liver fibrosis was promoted and reticular fiber was strongly stained by silver impregnation (FIG. 3, left). Staining of reticular fiber was weakened and normalized by the administration of a CBP/β-catenin inhibitory compound (FIG. 3, right).

Similarly, promoted liver fibrosis due to chronic hepatitis and strong staining of collagenous fibers by Azan staining were normalized by the administration of a CBP/β-catenin inhibitory compound and the staining was weakened (FIG. 4).

From the above results, it was clarified that a CBP/β-catenin inhibitor has a defibrosing action on chronic hepatitis, hepatic fibrosis or cirrhosis.

INDUSTRIAL APPLICABILITY

A CBP/β-catenin inhibitor is useful as a prophylactic and/or therapeutic agent for hepatic fibrosis.

This application is based on patent application No. 2012-270987 filed in Japan, the contents of which are encompassed in full herein.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A method for the prophylaxis or treatment of hepatic fibrosis, comprising administering an effective amount of a CBP/β-catenin inhibitor to a mammal, wherein the CBP/β-catenin inhibitor is selected from:
   4-(((6S,9S,9aS)-1-(benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen phosphate, and
   (6S,9S,9aS)-N-benzyl-6-(4-hydroxybenzyl)-2,9-dimethyl-4,7-dioxo-8-(quinolin-8-ylmethyl)octahydro-1H-pyrazino[2,1-c][1,2,4]triazine-1-carboxamide,
   and wherein the hepatic fibrosis is selected from alcoholic hepatopathy, autoimmune hepatopathy, drug-induced hepatopathy and metabolic hepatopathy.

2. The method according to claim 1, wherein the hepatic fibrosis is caused by non-alcoholic steatohepatitis.

* * * * *